US008812249B2

(12) United States Patent
Spiteri (10) Patent No.: US 8,812,249 B2
(45) Date of Patent: Aug. 19, 2014

(54) ANALYZER APPARATUS AND METHODS FOR LUNG DISEASE

(75) Inventor: Monica Silverstone Spiteri, Stoke-on-Trent (GB)

(73) Assignee: University Hospital of North Staffordshire NHS Trust (GB)

( * ) Notice: Subject to any disclaimer, the term of this patent is extended or adjusted under 35 U.S.C. 154(b) by 662 days.

(21) Appl. No.: 12/506,864

(22) Filed: Jul. 21, 2009

(65) Prior Publication Data

US 2010/0332141 A1    Dec. 30, 2010

(30) Foreign Application Priority Data

Jun. 25, 2009    (GB) .................................. 0911007.3

(51) Int. Cl.
G01N 33/483    (2006.01)
G01N 33/48    (2006.01)
G06F 19/00    (2011.01)

(52) U.S. Cl.
CPC .......... *G06F 19/3487* (2013.01); *G06F 19/345* (2013.01); *G06F 19/363* (2013.01)
USPC .............................................. 702/22; 702/19

(58) Field of Classification Search
USPC .................................................. 702/19, 22
See application file for complete search history.

(56) References Cited

U.S. PATENT DOCUMENTS

| 6,972,172 B2* | 12/2005 | Dukler et al. ................ 435/6.11 |
| 2006/0211047 A1 | 9/2006 | Mutsuhiko et al. |
| 2007/0009970 A1* | 1/2007 | Heller et al. ................. 435/7.23 |
| 2008/0044843 A1* | 2/2008 | Perlee et al. .................... 435/24 |
| 2008/0133141 A1* | 6/2008 | Frost ................................. 702/19 |
| 2009/0171590 A1* | 7/2009 | Puskas et al. ................... 702/19 |
| 2009/0215734 A1* | 8/2009 | Gerhart ......................... 514/171 |
| 2010/0070191 A1* | 3/2010 | Gold et al. ...................... 702/19 |
| 2010/0088264 A1* | 4/2010 | Teverovskiy et al. .......... 706/46 |
| 2011/0160070 A1* | 6/2011 | Gervais et al. .................... 506/8 |

FOREIGN PATENT DOCUMENTS

| EP | 1 211 326 A2 | 6/2002 |
| EP | 1 806 581 A1 | 7/2007 |
| WO | WO0015020 A1 | 3/2000 |
| WO | WO0158338 A2 | 8/2001 |

(Continued)

OTHER PUBLICATIONS

Clin Exp Allergy, vol. 35, 2005, JL Simpson, et al., "Inflammatory mediators in exhaled breath, induced sputum and saliva", 1180-1185.

(Continued)

*Primary Examiner* — Michael Nghiem
*Assistant Examiner* — Alexander Satanovsky
(74) *Attorney, Agent, or Firm* — Shumaker, Loop & Kendrick, LLP (57) ABSTRACT

An apparatus arranged to give an output indicative of lung disease state, in particular Chronic Obstructive Pulmonary Disease (COPD). The apparatus comprises a biomarker detection unit; a patient information input unit; a memory unit; a processing unit; and an output unit. The biomarker detection unit generates biomarker information by analyzing a patient saliva sample. The biomarker information is processed with patient information relating to patient symptoms, and an appropriate output generated based on the combination of the biomarker information and the patient information. The output suitably indicates whether there is a change in the disease state, and may further include a recommendation regarding treatment for the disease according to such a change.

21 Claims, 9 Drawing Sheets

(56) References Cited

FOREIGN PATENT DOCUMENTS

| WO | 03/003274 A1 | 9/2003 |
|---|---|---|
| WO | 2005/064517 A1 | 7/2005 |
| WO | 2005/087091 A2 | 9/2005 |
| WO | 2006067427 A2 | 6/2006 |
| WO | 2006085984 A3 | 8/2006 |
| WO | 2006121510 A3 | 11/2006 |
| WO | WO2006/118522 A1 | 11/2006 |
| WO | WO2007084485 A1 | 7/2007 |
| WO | 2008003066 A2 | 1/2008 |
| WO | 2008051260 A1 | 5/2008 |
| WO | WO2008064684 A1 | 6/2008 |
| WO | WO2008079322 A1 | 7/2008 |
| WO | 2008/120011 A1 | 10/2008 |
| WO | WO2008124010 A1 | 10/2008 |
| WO | 2009114292 A1 | 9/2009 |

OTHER PUBLICATIONS

International Search Report from the European Patent Office for PCT/GB2010/051061 dated May 10, 2010.
United Kingdom Search Report for GB Patent Application No. 0911007.3 dated Feb. 4, 2010.

* cited by examiner

FIGURE 1

10 - Biomarker detection unit

20 - Patient information input unit

30 - Memory unit

40 - Processing unit

50 - Output unit

COPD PROFILE

| COPD History: Duration _____ (Yrs) | |
|---|---|
| Smoking Habit?<br>• Never smoked<br>• Current smoker<br>• Ex-smoker<br><br>Shortness of Breath: At rest Y / N ; On exertion Y / N<br><br>MRC Dyspnoea Scale: Grade _______<br><br>Body Mass Index (BMI): _______ | |
| Other Respiratory Illnesses? - Y / N<br>TB - Y / N<br>Bronchiectasis - Y / N<br>Other : _______ | Childhood Respiratory Symptoms:<br><br>Y / N / don't know |
| Other Known Medical Conditions?<br><br>Heart Failure - Y / N          Diabetes - Y / N<br>MI - Y / N                     Hypertension - Y / N<br>Angina - Y / N | |

| Respiratory Mode | Inhaled | Nebulised | Oral |
|---|---|---|---|
| B2 agonist<br>  Short Acting<br>  Long Acting | | | |
| Anticholinergic<br>  Short Acting<br>  Long Acting | | | |
| Steroid | | | |
| Theophyllines | | | |

How many hospital admissions have you had
with COPD in the last 12 months?       _______

| Flare-up episode in last 12 months | 0 | 1-3 | 4-6 | 7-9 | 10+ |
|---|---|---|---|---|---|
| | | | | | |

FIGURE 2

Well Being & Life Impact Score

HOW IS YOUR BREATHING TODAY?
- 1 = EXCELLENT
- 2 = GOOD
- 3 = FAIR
- 4 = BAD
- 5 = VERY BAD

IS THIS?
- 1 = MUCH BETTER THAN USUAL
- 2 = BETTER THAN USUAL
- 3 = USUAL
- 4 = WORSE THAN USUAL
- 5 = MUCH WORSE THAN USUAL

HOW IS YOUR ABILITY TO PERFORM THESE DAILY ACTVITIES TODAY?

|  | NOT AT ALL = 1 | A LITTLE = 2 | A FAIR AMOUNT = 3 | MUCH = 4 | VERY MUCH = 5 |
|---|---|---|---|---|---|
| Perform activities of daily living<br>- Self-washing<br>- Self-dressing<br>- Cooking<br>- Housework |  |  |  |  |  |
| Do you work? - Y / N<br><br>If Yes,<br>How does COPD affect your work? - |  |  |  |  |  |
| Physical activities<br>Housebound<br>- Y / N<br>If No →<br>- Shopping<br>- Walking<br>- Gardening<br>- Swimming<br>- Cycling<br>- Dancing<br>- Other |  |  |  |  |  |

FIGURE 3

COUGH & SPUTUM SCORE

Do you have a cough? Y / N
If Yes, is this?

- 1 = MUCH BETTER THAN USUAL
- 2 = BETTER THAN USUAL
- 3 = USUAL
- 4 = WORSE THAN USUAL
- 5 = MUCH WORSE THAN USUAL

Do you expectorate sputum (mucus)? Y /N
If Yes,

How much sputum do you produce each day?
1 = UP TO 5mls (1 teaspoon)
2 = UP TO 10mls (2 teaspoons)
3 = UP TO 15mls (1 tablespoon)
4 = UP TO 30mls (1 egg cup)
5 = ABOUT OR GREATER THAN 50mls (1 cup or above)

What is the texture of your sputum ?
1 = WATERY
2 = WATERY + FROTHY
3 = STICKY LIQUID
4 = SEMI-SOLID
5 = SOLID What is the colour of your sputum?

Sputum Colour Score

| watery, clear and transparent | Watery, cloudy and colourless | Creamy |
|---|---|---|
| 1 | 2 | 3 |
| Pale green | Dark green | |
| 4 | 5 | |

BIOMARKER SCORES

SCORES

NORMAL ☑ ◄─────────────► ABNORMAL ☒

| TARGET BIOMARKER | 1 | SLIGHT 2 | MODERATE 3 | MUCH 4 | VERY MUCH 5 |
|---|---|---|---|---|---|
| CRP | | | | | |
| PROCALCITONIN | | | | | |
| NEUTROPHIL ELASTASE | | | | | |
| IL-8 | | | | | |
| MYELOPEROXIDASE | | | | | |

ANALYZER APPARATUS AND METHODS FOR LUNG DISEASE

CROSS-REFERENCE TO RELATED APPLICATIONS

This application claims priority to International Application No. GB/0911007.3 filed Jun. 25, 2009, the contents of which are incorporated by reference herein.

TECHNICAL FIELD AND BACKGROUND OF THE INVENTION

The present invention relates to testing apparatus and methods useful in connection with lung disease, in particular but not exclusively chronic obstructive pulmonary disease (COPD).

Biomarkers whose regulation is perturbed in lung disease patients have been used to diagnose and aid treatment of lung diseases such as COPD. Typical biomarkers comprise protein analytes, collected from patient sputum and tested using reagent kits. Such analytes also exist in serum, bronchial samples and saliva and may be tested in other ways, for example using immunoassays or microarrays. However, there is little known correlation between levels of typical biomarkers and the day to day wellbeing of patients with or susceptible to lung disease.

BRIEF SUMMARY OF THE INVENTION

In a first aspect, the present invention provides an apparatus arranged to give an output indicative of lung disease state, the apparatus comprising:

a patient information input unit arranged to receive patient information input thereto;

a biomarker detection unit arranged to receive a sample from a patient, to detect a biomarker in the sample and to generate biomarker information in response to a detected biomarker;

a memory unit to store the biomarker information and the patient information;

a processing unit arranged to operate on the biomarker information and the patient information in the memory unit to determine a lung disease state for the patient, and an output unit arranged to provide an output indicative of lung disease state according to the determination made by the processing unit.

Suitably, the patient information comprises information relating to the patient's perceived own symptoms. Suitably, the patient information comprises information relating to the patient's perceived own lung function. Suitably, the patient information comprises patient-reported information. Suitably, the patient information comprises a plurality of scores relating to clinical indicators of lung disease state.

Suitably, the biomarker information comprises information indicative of the presence of, or a change in the expression level of one or more of: C-reactive protein, neutrophil elastase, IL-8, myeloperoxidase and procalcitonin.

Suitably, the biomarker detection unit is arranged to receive a sample comprising one or more of: blood, serum, sputum, breath and saliva. Suitably, the biomarker detection unit comprises a lab on chip unit.

Suitably, the memory unit is arranged such that patient information stored therein is associated with timing data relating to the time at which: the patient information is received; or the patient information is stored. Suitably, the memory unit is arranged to store a plurality of determined disease states, and timing data relating to the time at which each determination was made.

Suitably, the memory unit is arranged to store a plurality of pieces of biomarker information relating to a corresponding plurality of samples received over time from a patient. Suitably, the memory unit is arranged to store a plurality of pieces of patient information received over time from a patient. Suitably, the memory unit is arranged such that biomarker information stored therein is associated with timing data relating to the time at which: the sample is received; the biomarker information is generated; or the biomarker information is stored.

Suitably, the memory unit is arranged to store a sequence of biomarker information and/or patient information recorded over time.

Suitably, the processing unit is arranged to operate on more than one piece of biomarker information stored in the memory unit. Suitably, the processing unit is arranged to operate on more than one piece of patient information stored in the memory unit. Suitably, the processing unit is arranged to operate on a sequence of biomarker information and/or patient information recorded over time. Suitably, the processor unit is arranged to operate on more than one previously determined disease state stored in the memory unit.

Suitably, the output unit is arranged to provide an output indicative of lung disease state according to the determination made by the processing unit, the output indicating the state as either stable or changing. Suitably, the output unit is arranged to provide an output indicative of the initiation of a COPD-related disease response. Suitably, the output unit is arranged to provide an output indicative of further clinical action to be taken in response to the determination made by the processing unit.

Suitably, the output unit is arranged to produce a local output to a local user, and/or is arranged to transmit information from the apparatus to a remote monitoring station. Suitably, the units are provided in a single integrated apparatus.

In a second aspect the present invention provides a method of generating an output indicative of lung disease state, the method comprising:

receiving, at a patient information input unit, patient information;

receiving, at a biomarker detection unit, a patient sample;

detecting a biomarker in the sample and generating biomarker information in response to the detected biomarker;

storing the biomarker information and the patient information in a memory unit;

operating on the biomarker information and the patient information in the memory unit to determine a lung disease state for the patient, and providing an output indicative of the so-determined lung disease state.

Suitably, the method further comprises generating a clinical score based on the received patient information.

In a third aspect the present invention provides a method of identifying an individual having lung disease that is responsive to a treatment for said lung disease, the method comprising steps of: determining a lung disease state for the individual; providing a treatment appropriate to the lung disease state; monitoring the lung disease state according to the method of the second aspect of the present invention or using the apparatus of the first aspect of the invention; and identifying the individual as responsive to the treatment according to changes in the monitored disease state.

In a fourth aspect the present invention provides a method of assaying the efficacy of a treatment for lung disease in an individual, said method comprising steps of: identifying an individual having lung disease; determining a lung disease state for the individual; providing a treatment; monitoring the lung disease state according to the method of the second aspect of the present invention or using the apparatus of the first aspect of the invention; and identifying the treatment as effective according to changes in the monitored disease state.

BRIEF DESCRIPTION OF THE DRAWINGS

For a better understanding of the invention, and to show how embodiments of the same may be carried into effect, reference will now be made, by way of example, to the accompanying diagrammatic drawings in which.

DETAILED DESCRIPTION OF THE PREFERRED EMBODIMENT AND BEST MODE

Diseases of the lung, such as COPD are complex diseases with a relatively wide spectrum of severity and co-morbidity. At present disease monitoring is typically performed by a clinician.

In treatment of lung disease such as COPD it is generally desirable to be able to predict flare-ups at an early stage, and to be able to recognize changes to disease status over time for an individual patient within a treatment program. An apparatus for determining the status of COPD at any given time and comparing status as it changes over time through an interactive analysis of information derived from disease-relevant patient-reported health events and biological markers ideally in saliva is proposed in example embodiments of the present invention. Furthermore, example embodiments are arranged to produce feedback messages relevant to COPD status and treatment regimes to a user and to a clinician. Such embodiments may suitably improve diagnostic accuracy. Furthermore the level of remedial action at point-of-care may suitably be directed according to so-determined status changes and/or knowledge of the history of COPD status for the particular patient.

To enhance utility of patient-reported events, as well aid in correctly apportioning patient-reported events to COPD disease process, example embodiments combine assessment of information received from a patient with disease-related biological events occurring within said patient, i.e. biomarker information is used in conjunction with patient information.

As COPD progresses, COPD pathogenesis is likely to be an evolution of local and systemic inflammatory and/or infective events occurring first at body tissue level before visible clinical and functional changes set in. To capture information on these events in a near-patient setting, apparatus according to example embodiments incorporates miniaturized systems such as a multi-analyte assay platform (for example a lab-on-chip arranged for measurement of a group of COPD-relevant biomarkers). The apparatus is arranged for non-invasive self-testing of easily accessible biological fluids such as saliva or sputum. The group of biomarkers chosen may suitably include those relevant to pathogenesis of the disease, that are measurable in saliva or sputum, that reflect early fluctuations in disease condition, and are preferably but not necessarily discriminatory of a particular state for example COPD.

Figure 1:
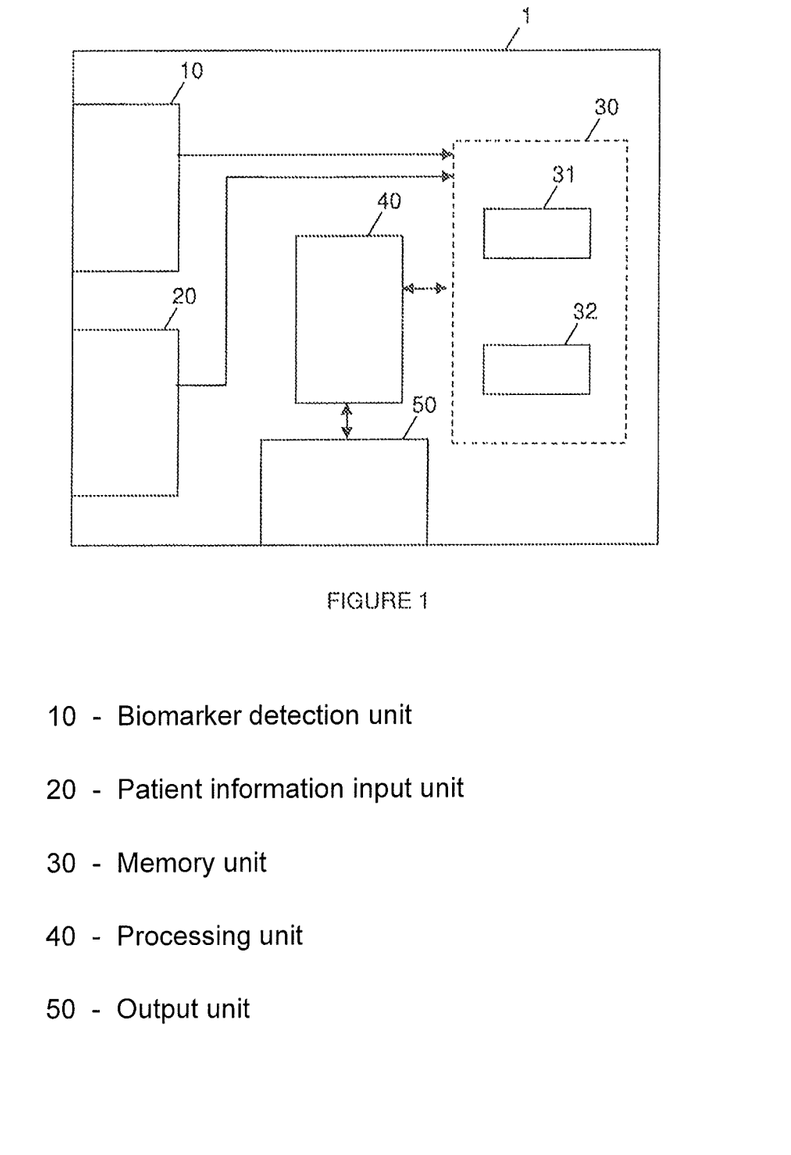
FIG. 1 shows a schematic view of an apparatus arranged to give an output indicative of lung disease state, according to an example embodiment of the present invention.

FIG. 1 shows a schematic view of an apparatus 1 arranged to give an output indicative of lung disease state, according to a first example embodiment of the present invention. The apparatus of FIG. 1 comprises a biomarker detection unit 10; a patient information input unit 20; a memory unit 30; a processing unit 40; and an output unit 50.

The biomarker detection unit 10 is arranged to receive a saliva sample from a patient, to detect biomarkers in the sample and to generate biomarker information in response to one or more detected biomarkers. In this example embodiment the biomarker detection unit 10 is arranged to detect C-reactive protein, neutrophil elastase, IL-8, myeloperoxidase and procalcitonin. However, other suitable biomarkers may be included, or some from this list substituted for others or not detected.

The patient information input unit 20 is arranged to receive patient information input thereto, such as by a patient. The patient information input unit 20 comprises a touch screen, display and keypad or other suitable input device. The patient information suitably comprises one or more of self-reported health scores relating to: day-to-day activity; breathing; cough; sputum amount, texture and colour.

The memory unit 30 is arranged to store, patient information and biomarker information. The memory unit 30 comprises a number of storage areas. In a first storage area 31 a database including current and historical patient and biomarker information is stored. The database further includes timestamps indicating the time at which each piece of biomarker information was generated and the time at which each piece of patient information was received. The database may also include results of previous disease state determinations. In a second storage area 32 the memory unit 30 stores data used to control and inform operation of the processing unit 40, as described below.

The processing unit 40 is arranged to operate on information in the memory unit 30, in particular the biomarker information and the patient information in the memory unit 30 to determine a lung disease state for the patient. The processing unit 40 loads the biomarker information and patient information from the first memory area 31 of the memory unit 30 and operates thereon according to control data loaded from the second memory area 32 of the memory 30. As a result of the operations of the processing unit 40 a lung disease state is determined and passed to the output unit 50. The determined disease state may be stored in the memory unit 30 to be available for later use, for example to be used in combination with the biomarker and patient information in determining a disease state at a future time.

The output unit 50 comprises a communication capability for transferring data from the apparatus to either a local user or a remote location, or both. For example, as well as providing a local user with immediate feedback via a screen, according to the determined lung disease state, the output unit 50 may enable remote transmission of the disease state and/or other information from the apparatus 1 to a clinic. This enables the determined lung disease state to be regularly and quickly assessed by a clinician to thereby improve care.

The decision making processes that inform the operation of the processing unit 40 to enable a determination of lung disease state to be made are described in more detail below.

Figure 2:
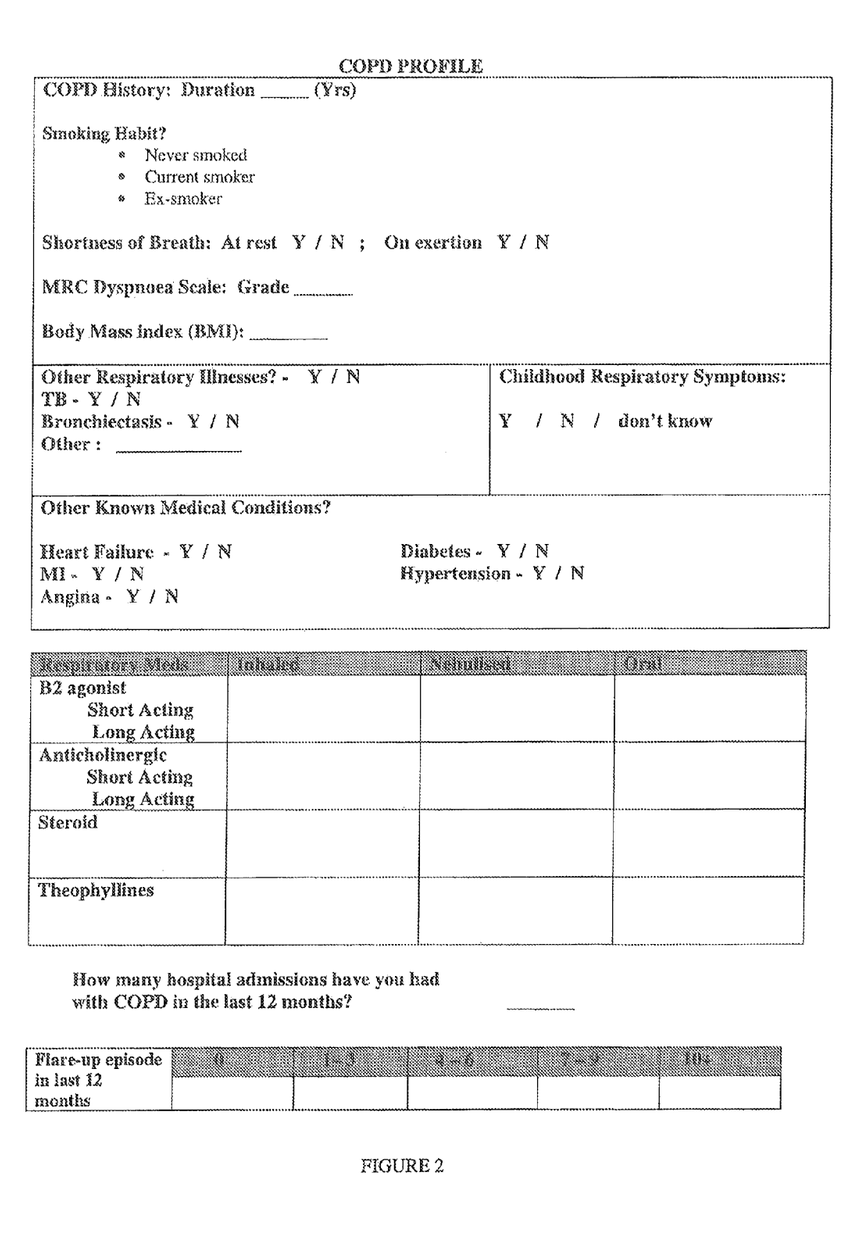
FIGS. 2-4 shows an example screen shot illustrating types of patient information gathered in an apparatus according to an example embodiment of the present invention.

Initially, a patient is diagnosed by a clinician, and general demographic information relating to the patient and the disease state at diagnosis are input via the patient information input unit 20 for storage in the memory unit 30. This input may take place on first diagnosis, or on first use of the apparatus by a previously diagnosed patient. Examples of the types of patient information gathered at this step are given in an example screen shot as shown in FIG. 2.

The first set of patient information, for example received under guidance from a clinician, and combined with an assessment of biomarkers at that time are used to determine an initial COPD status, for example a rating on a scale of 0 to 5, or on a scale including graded statuses mild, moderate, severe or severe plus. In addition to the severity level, the disease may be determined to have stable or unstable status.

COPD patients typically have day-to-day symptom variation and/or particular biomarker fluctuations which do not necessarily reflect a change in disease state and/or need changes to be made to a treatment plan. By making use of time-stamped data in the first memory area 31 of the memory unit 30 the processing unit 40 is arranged to be sensitive to changes in patient information and biomarker information of the particular patient. In this way changes to disease state are of particular interest, as even small to moderate fluctuations in severe COPD state may be more critical than relatively larger fluctuations in patients with milder COPD states.

Building up the data in the first memory area 31 of the memory unit 30 enables personal patterns of COPD disease state to emerge, and these patterns are recognizable by the processing unit 40. Individual day-to-day levels of variation are determined with reference to the data in the first memory area 31 of the memory unit 30. Then, the processing unit 40 considers cumulative magnitude changes in biomarker and patient information as percentages to baseline, their rate of alteration and their rate of alteration relative to one another. Using these considerations disease state is determined. By considering changes relative to a baseline more accurate determination is made possible, for example in cases where the patient is already symptomatic and has biomarker information indicating abnormal levels of one or more biomarkers at presentation.

Figure 3:
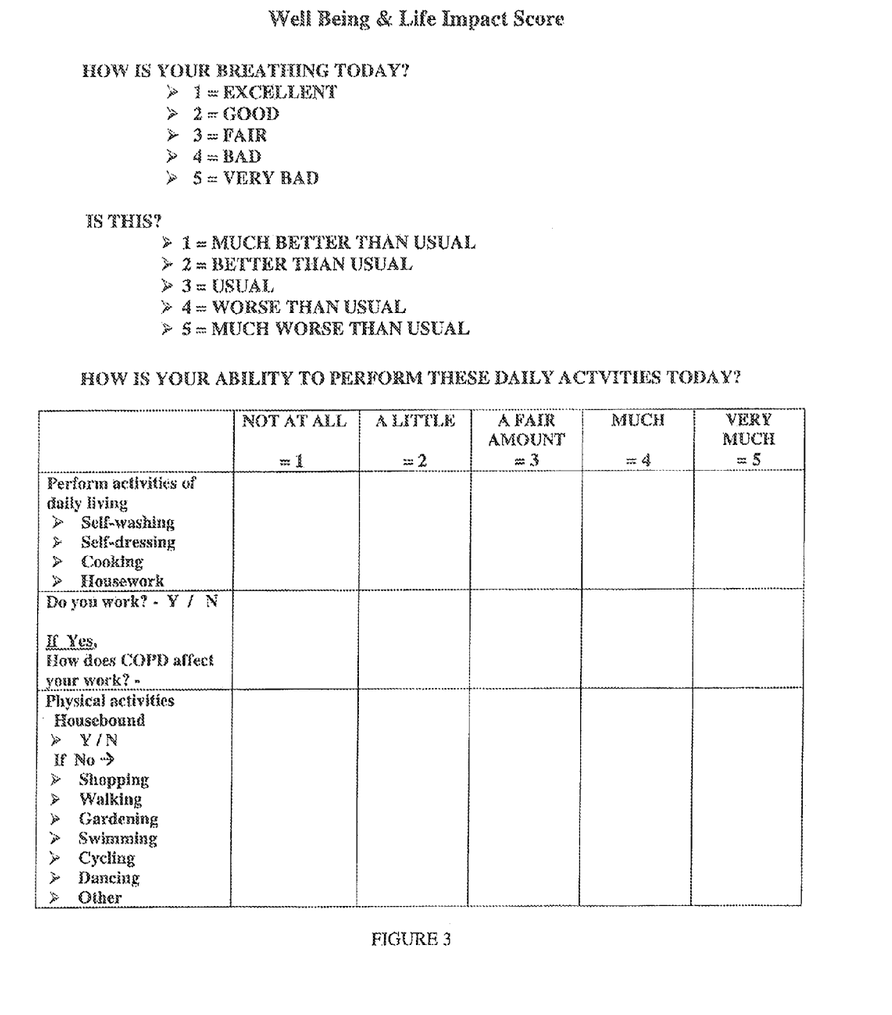
Figure 4:
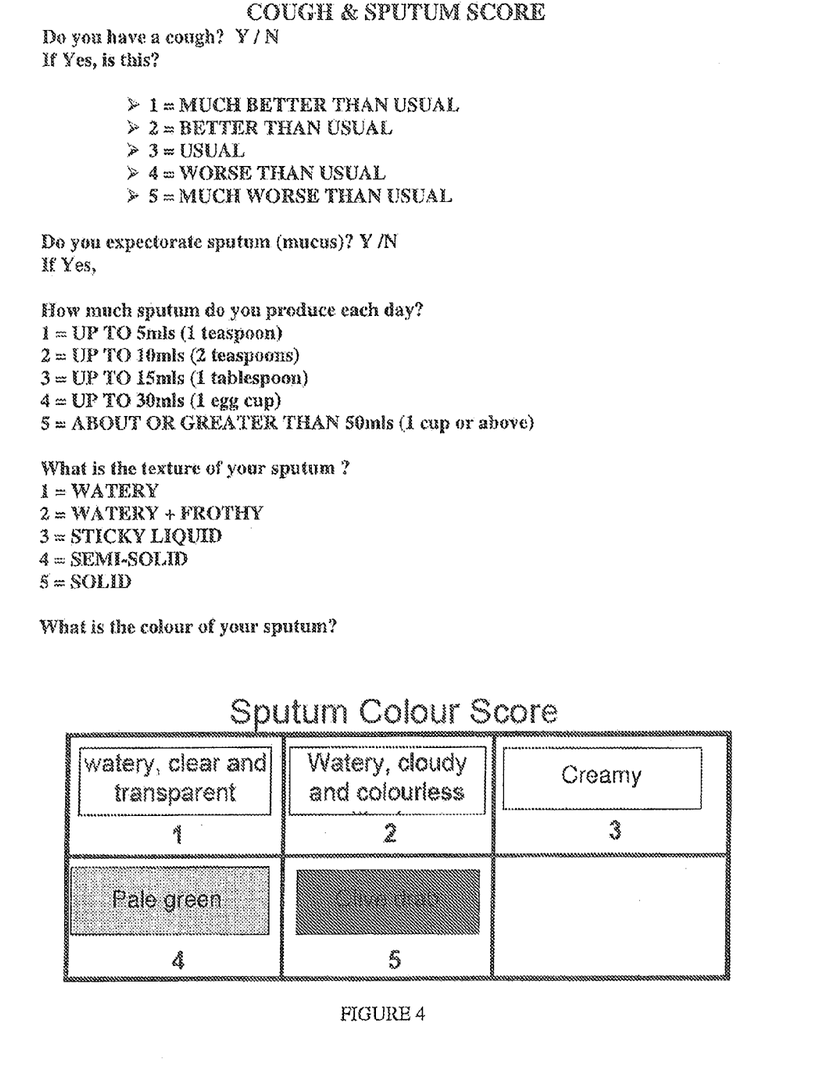

Factors considered as relevant patient information are shown in FIGS. 3 and 4, which represent example screen shots relating to gathering of patient information. To simplify processing, patient information may conveniently be collected and scored according to a five point scale.

For biomarker information measured shifts from baseline are for example stratified into five levels depending on percentage change range in each biomarker of interest.

Interpretation of the scores in the processing unit 40 may be adjusted according to the baseline expected for a patient with a previously determined disease. Table 1 shows an example matrix by which patient information and biomarker information may be combined.

TABLE 1

| | | SEVERITY SCALE | | | | |
|---|---|---|---|---|---|---|
| | | 1 | 2 | 3 | 4 | 5 |
| Patient Information | Breathing Daily activity Cough Sputum | | | | | |
| Biomarker Information | CRP Procalcitonin Neutrophil Elastase IL8 Myeloperoxidase | | | | | |

Factors to consider when combining patient information with biomarker information may for example include: severity of airflow obstruction, dyspnoea score scale, body mass index, number of acute episodes in previous year, co-morbidity presence, normal or abnormal C-reactive protein level or other biomarker or parameter. For example, a mild stable COPD rating would reflect a status whereby an individual is not troubled by breathlessness on exertion, whose airflow obstruction is greater than 80% of his predicted, less than 3 acute non-hospitalized episodes a year and normal baseline C-reactive protein level and/or other biomarker levels. This status would change to mild unstable COPD if for example there is hospitalization in course of a year, or a persistently abnormal C-reactive protein level and/or other biomarker levels or other co-morbid conditions. An individual may move up the scale depending on a personalized scaling provided for the different parameters and scores.

For example, as well as raised levels of biomarkers, a differential pattern in expression levels of each marker could indicate a change from a stable to an unstable state, or an inflammatory event or absence or presence of a bacterial infection or pneumonia before the onset of significant change in symptoms.

Figure 5:
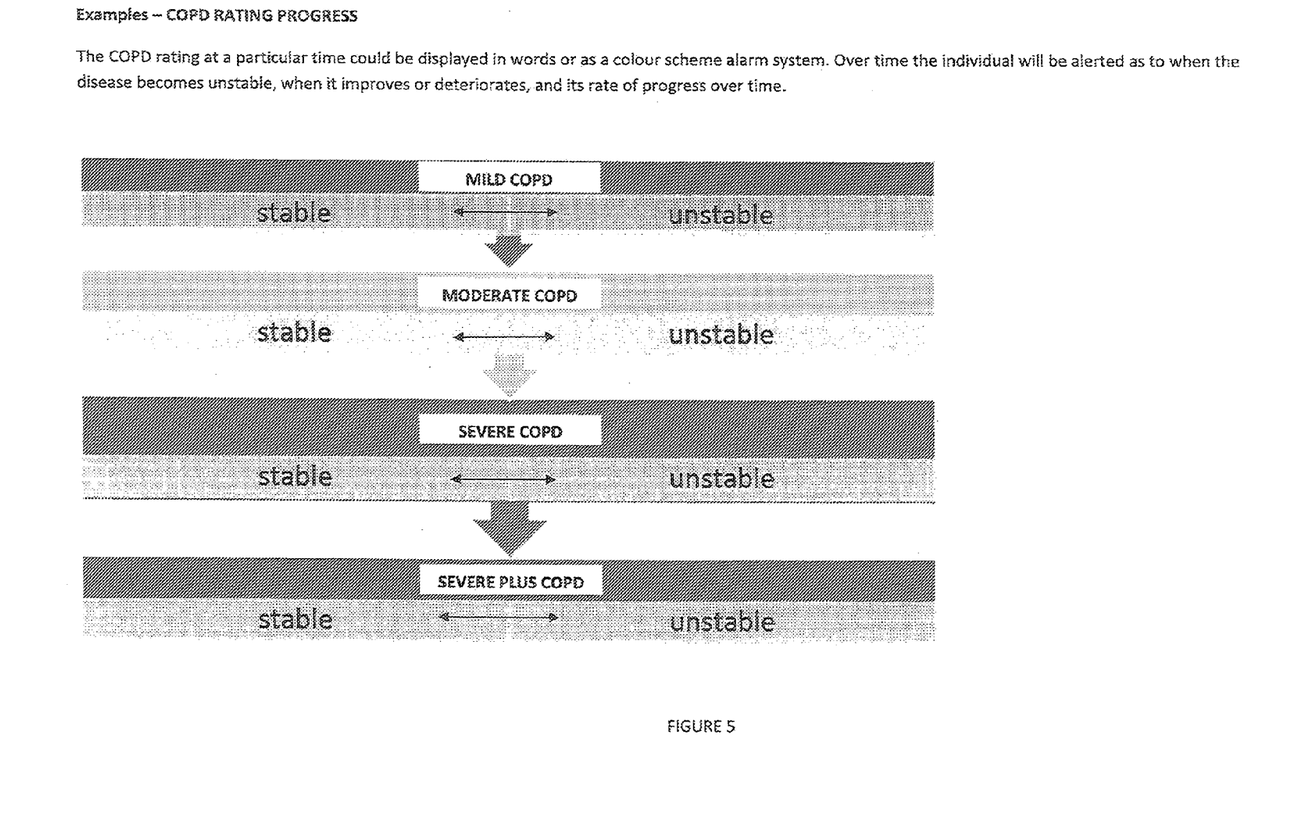
FIG. 5 shows an example screen shot illustrating types of status indications that may be given by an apparatus according to an example embodiment of the present invention.
Figure 6:
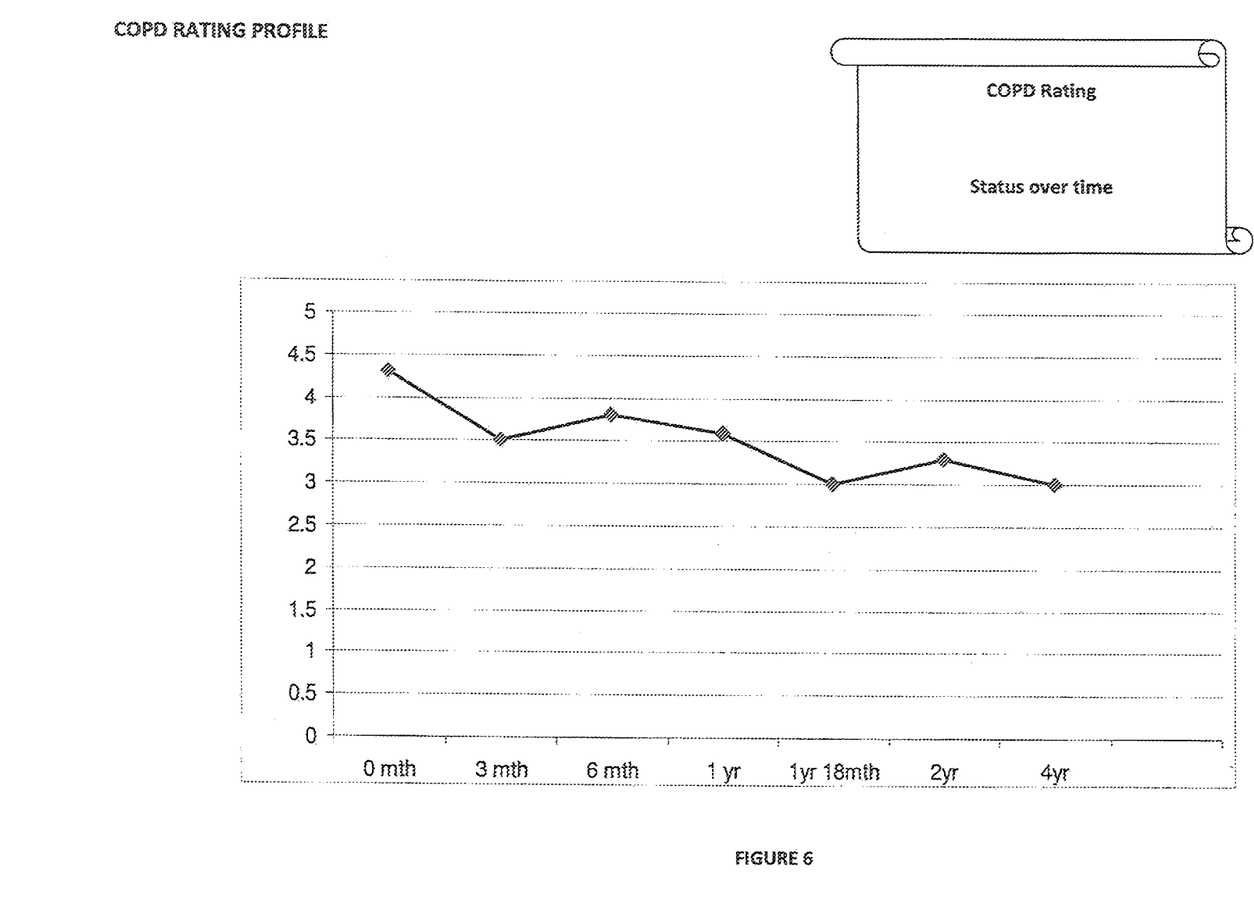
FIG. 6 shows an example screen shot illustrating a historical chart of status indications generated over time presented on an apparatus according to an example embodiment of the present invention.

From the determined disease state the output unit 50 may present, in real time, simple visual feedback indicative of a disease state or changes to a disease state. FIG. 5 shows an example of a display showing the range of status indications that may be given in example embodiments. A historical chart of status indications generated over time may also be generated, for example as shown in FIG. 6

Figure 7:
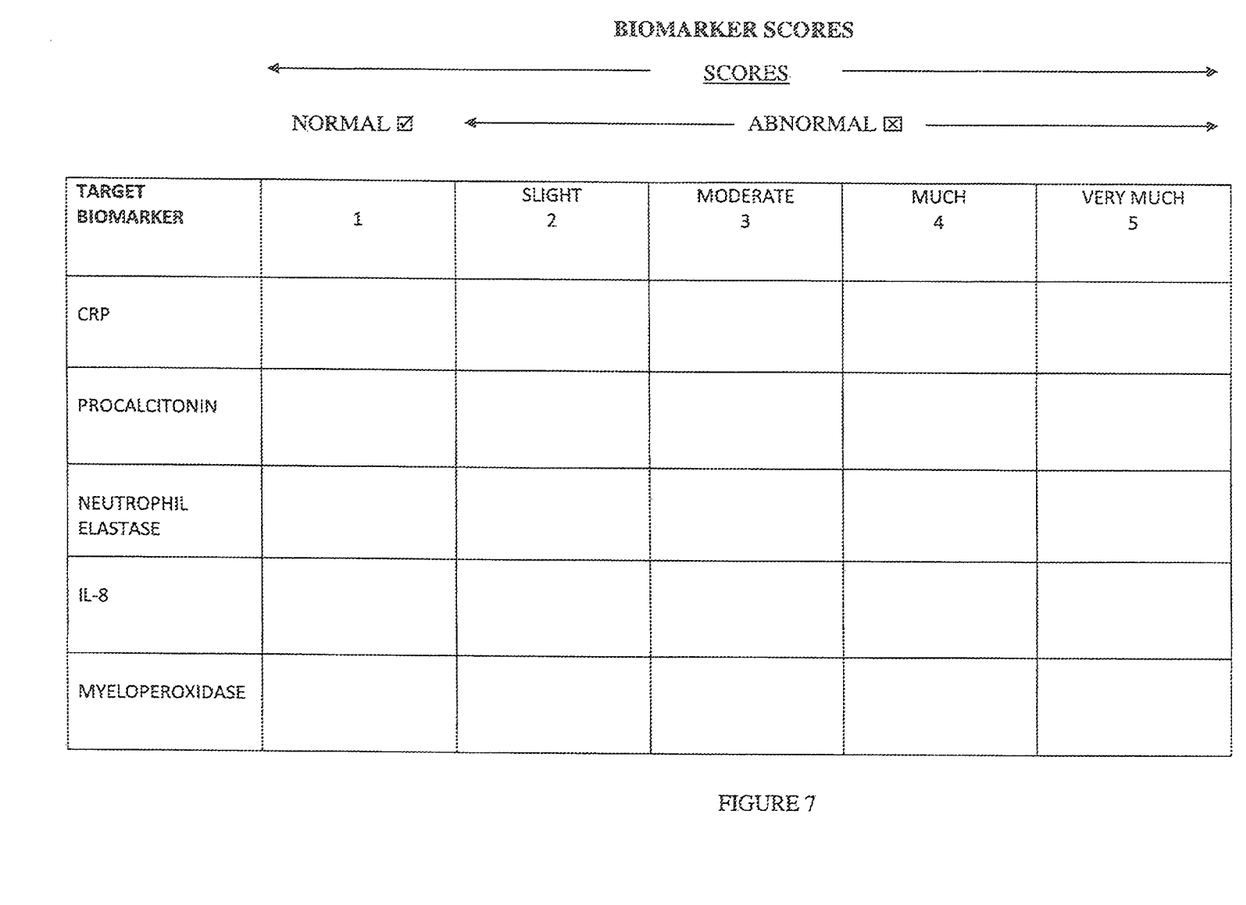
FIG. 7 shows an example screen shot illustrating detailed feedback relating to the biomarker information presented on an apparatus according to an example embodiment of the present invention.

More detailed feedback relating to the biomarker information may also be provided, as exemplified by FIG. 7. FIG. 7 shows an example table of biomarker feedback results for each biomarker, defined as normal or abnormal, and within the latter four scales of severity to reflect and indicate the percentage change from normal level. A readout report for each biomarker result is for example automatically displayed symbolically as ☑ (a box with a checkmark therethrough) for normal levels or ☒ (a box with an x-mark therethrough) for levels that are abnormal, with the symbol appearing against the appropriate scale of severity. Such feedback may be useful to a clinician.

Figure 8:
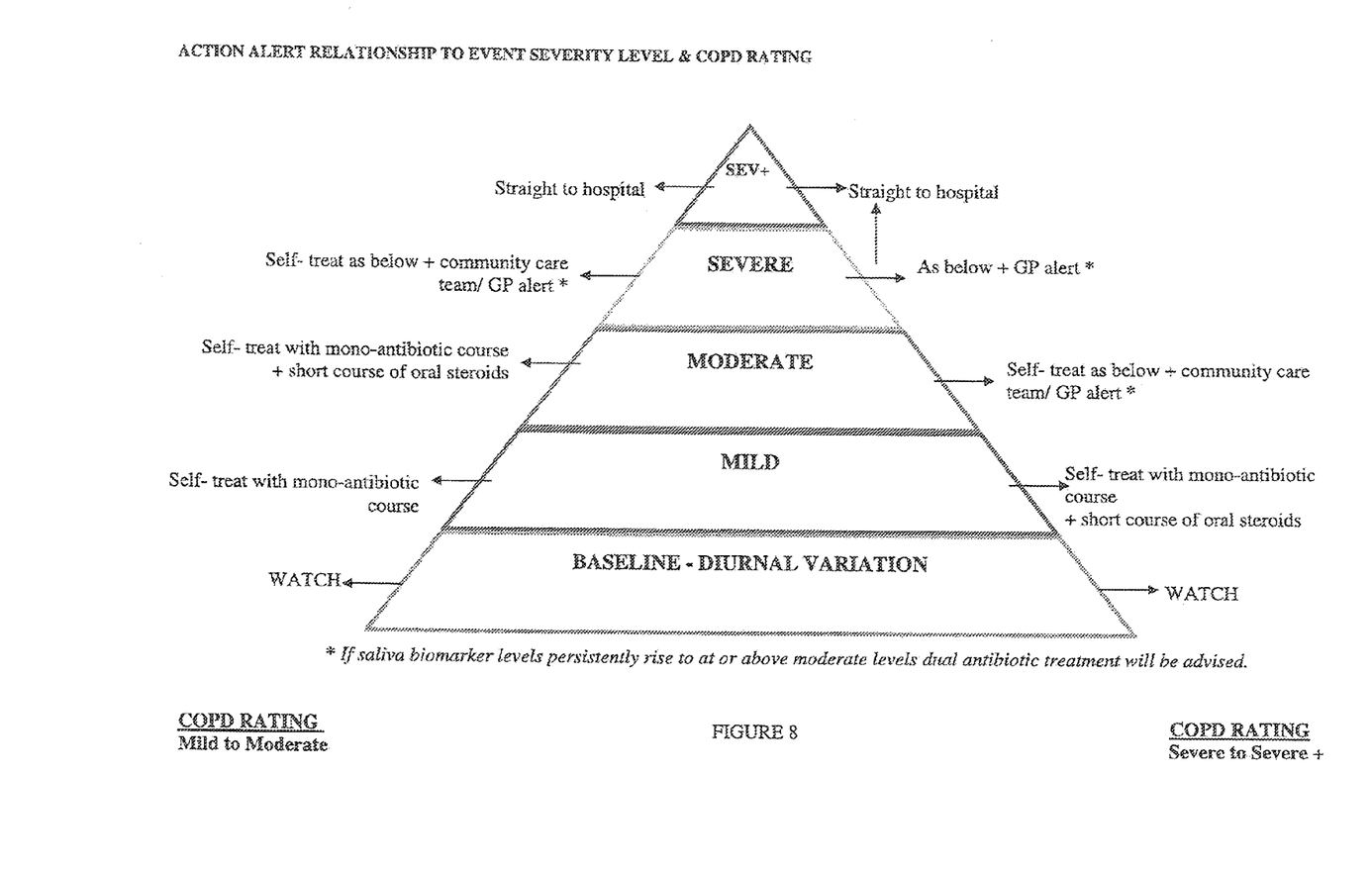
FIG. 8 shows an action alert model used in example embodiments of the present invention for relating changes in disease status to changes in treatment plans.

Instructions to a local user or to a remote clinician relating to desirable clinical steps to be taken in light of the determined disease state, or in light of a change in the disease state relative to previous determined disease states may also be indicated, based on an action alert model as exemplified in FIG. 8.

In cases where there are minor changes in symptoms and/or biomarker levels these could be within the day to day fluctuations and thus no change in disease state is registered and no clinical action needed. If however such minor changes persist over a longer period of time and involve changes in major patient information or biomarker information, especially for patients previously identified as of severe to severe plus COPD rating, then a step-up in treatment may be all that is needed. For example if the patient is on inhaled steroids, treatment may involve an increased steroid dosage or treatment with a short course of antibiotics.

In cases where there are minor changes in biomarker information but not in patient information then the disease state is unlikely to have changed. In this situation further clinical intervention may not be needed. If changes in biomarker level are moderate and above, especially if level changes occur persistently over time in more than one marker and one or more of the markers are major determinants for the patient, then the change to the disease state could trigger a step-up in treatment or short course of antibiotic or scale-up in antibiotic strength depending on level of change. This scenario could happen in early warning of flare-ups, in particular before a deterioration of symptoms is noticed by a patient.

Changes in patient information without changes to biomarker information are unlikely, aside from diurnal changes in symptoms which are part of daily disease fluctuation. In such cases further clinical intervention is unlikely to be required. If the patient information reflects new symptoms, i.e. there are changes reflected in the patient information that are not related to the usual respiratory symptoms, then clinical intervention to diagnose new ailments may be required. For example, sudden onset of chest pains suggests further medical examination by a clinician should be carried out.

Where changes in both patient information and biomarker information are detected, the judgement of what treatment is required is for example made dependent on the relative changes of one to the other. For example, small changes in patient information and biomarker information initially indicate no major change in disease state, meaning that further clinical intervention is unlikely to be needed at this stage. However, major changes in one or more piece of patient information or biomarker information coupled with only minor changes is more likely to represent a change in disease state. By extension, alerts may be scaled up if simultaneous major changes are encountered, with the disease state and/or further action required determined according to relative levels of change.

In other example embodiments the output unit 50 may serve to allow two-way remote communication. Two way communications in such embodiments allow a clinician to give instructions to a user relating to changes to required treatment regimes. Two way communications also allow updating of the information in the second memory area 32 in the memory unit 30, for example to update or improve performance of the apparatus in light of relevant new clinical or technical information becoming available.

Figure 9:
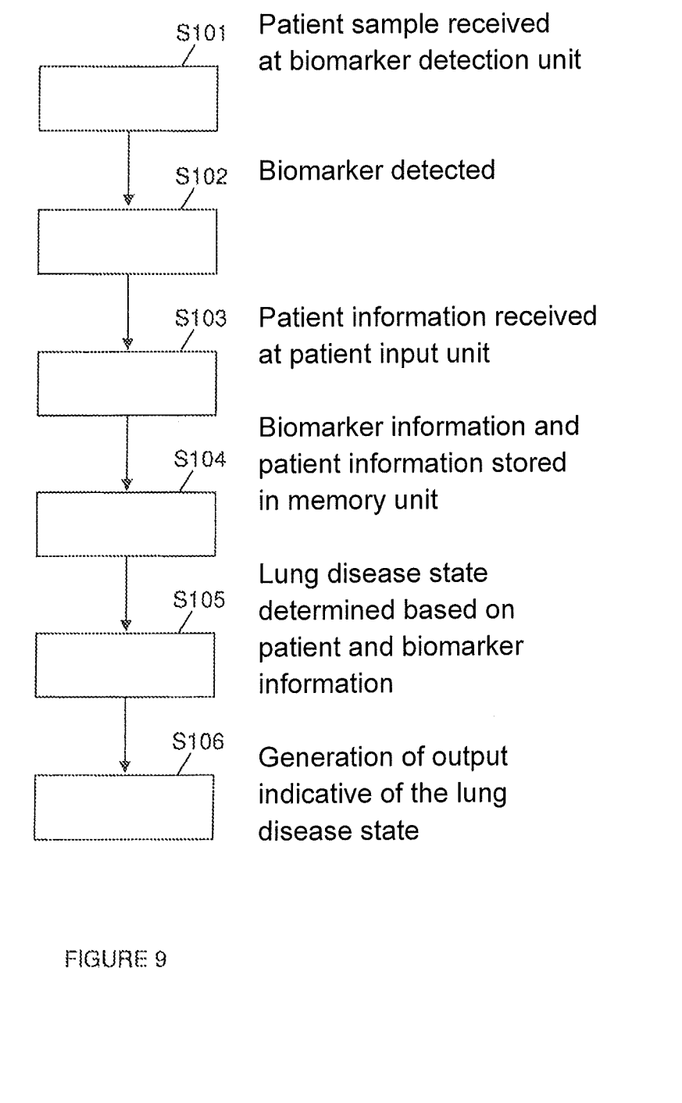
FIG. 9 shows an example flow diagram illustrating steps of a method of generating an output indicative of lung disease state according to an example embodiment of the present invention.

FIG. 9 shows an example flow diagram illustrating steps of a method of generating an output indicative of lung disease state according to an example embodiment of the present invention.

At step S101 a patient sample is received at a biomarker detection unit. Typically the patient sample is a saliva sample provided by the patient directly by the patient, without outside assistance.

At step S102 biomarkers are detected in the sample and in response biomarker information is generated.

At step S103 patient information is received at a patient information input unit. Typically the patient information comprises a set of data provided directly by the patient and containing a set of responses to questions concerning the symptoms being experienced by the patient.

At step S104 the biomarker information and the patient information is stored in a memory unit. Step S103 may be performed before step S101 and S102, and equally step S104 may be performed interleaved with steps S101-S103.

At step S105 the biomarker information and the patient information is operated on to determine a lung disease state for the patient. The operation at step S105 may refer to the most recently stored biomarker and patient information, and optionally to baseline information and historical biomarker and patient information stored in the memory unit.

At step S106 an output indicative of the lung disease state determined at step S105 is generated.

Accordingly, the example embodiments described herein enable prediction of lung disease flare-ups at an early stage, and provide a way to recognize changes to disease status over time for an individual patient. These advantages, along with the ability to regulate treatment, to monitor treatment efficacy and to screen potential new treatments are particularly useful in dealing with COPD. The present invention is applicable for use in COPD and other lung diseases, herein defined as those affecting any of the organs involved with breathing. These include asthma, chronic bronchitis, asthma, bronchiectasis, pneumonia and respiratory infections as well as sleep-related disorders.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

What is claimed is:

1. An apparatus arranged to give an output indicative of the initiation of a chronic obstructive pulmonary disorder (COPD)-related disease response, the apparatus comprising:
   a patient information input unit arranged to receive patient information input thereto, the patient information comprising a plurality of scores relating to clinical indicators of lung disease state;
   a biomarker detection unit arranged to receive a sample from a patient, to detect a biomarker in the sample and to generate biomarker information in response to a detected biomarker, wherein the biomarker information comprises one or more scores determined with reference to a severity scale, wherein the biomarker detection unit comprises a lab on chip unit, and wherein biomarker detection unit is arranged to receive a sample comprising: sputum, breath, and saliva;
   a memory unit to store the biomarker information and the patient information;

a processing unit arranged to operate on the biomarker information and the patient information in the memory unit to determine a lung disease state for the patient; and an output unit arranged to provide an output indicative of lung disease state according to the determination made by the processing unit;

wherein the patient information includes a plurality of patient self-reported scores determined with reference to a severity scale, the scores relating to the patient's perceived own symptoms and/or lung function and comprising: an amount of coughing score; an amount of sputum produced score; a texture of sputum produced score; and a color of sputum produced score; and wherein the biomarker information comprises a plurality of scores determined from the sample with reference to a severity scale and relating to the presence of, or a change in the expression level of one or more of: C-reactive protein, neutrophil elastase, Il-8, myeloperoxidase, and procalcitonin; and wherein the severity scale of the patient self-reported scores and the severity scale of the biomarker scores each utilize a same set of discrete numbers.

2. The apparatus of claim 1, wherein the biomarker detection unit is arranged to also receive a sample comprising blood and/or serum.

3. The apparatus of claim 1, wherein the memory unit is arranged such that patient information stored therein is associated with timing data relating to the time at which: the patient information is received; or the patient information is stored.

4. The apparatus of claim 1, wherein the memory unit is arranged to store a plurality of determined disease states, and timing data relating to the time at which each determination was made.

5. The apparatus of claim 1, wherein the memory unit is arranged to store a plurality of pieces of biomarker information relating to a corresponding plurality of samples received over time from a patient.

6. The apparatus of claim 1, wherein the memory unit is arranged to store a plurality of pieces of patient information received over time from a patient.

7. The apparatus of claim 1, wherein the memory unit is arranged such that biomarker information stored therein is associated with timing data relating to the time at which: the sample is received; the biomarker information is generated; or the biomarker information is stored.

8. The apparatus of claim 1, wherein the memory unit is arranged to store a sequence of biomarker information and/or patient information recorded over time.

9. The apparatus of claim 1, wherein the processing unit is arranged to operate on more than one piece of biomarker information stored in the memory unit.

10. The apparatus of claim 1, wherein the processing unit is arranged to operate on more than one piece of patient information stored in the memory unit.

11. The apparatus of claim 1, wherein the processing unit is arranged to operate on a sequence of biomarker information and/or patient information recorded over time.

12. The apparatus of claim 1, wherein the processor unit is arranged to operate on more than one previously determined disease state stored in the memory unit.

13. The apparatus of claim 1, wherein the output unit is arranged to provide an output indicative of lung disease state according to the determination made by the processing unit, the output indicating the state as either stable or changing.

14. The apparatus of claim 1, wherein the output unit is arranged to provide an output indicative of the initiation of a COPD-related disease response.

15. The apparatus of claim 1, wherein the output unit is arranged to produce a local output to a local user, and/or is arranged to transmit information from the apparatus to a remote monitoring station.

16. The apparatus of claim 1, wherein the units are provided in a single integrated apparatus.

17. A method of identifying an individual having chronic obstructive pulmonary disorder (COPD) that is responsive to a treatment, the method comprising steps of: determining a COPD disease state for the individual; providing a treatment appropriate to the COPD disease state; monitoring the COPD disease state according to the apparatus of claim 1; and identifying the individual as responsive to the treatment according to changes in the monitored disease state.

18. A method of assaying the efficacy of a treatment for chronic obstructive pulmonary disorder (COPD) in an individual, said method comprising steps of: identifying an individual having COPD; determining a COPD state for the individual; providing a treatment; monitoring the COPD state according to the apparatus of claim 1; and identifying the treatment as effective according to changes in the monitored disease state.

19. A method of generating an output indicative of initiation of a chronic obstructive pulmonary disorder (COPD)-related disease response, the method comprising:
receiving, via a patient information input unit, patient information comprising a plurality of scores relating to clinical indicators of lung disease state;
receiving, via a biomarker detection unit having a lab on chip unit, a patient sample comprising: sputum, breath, and saliva;
detecting a biomarker in the sample and generating biomarker information in response to the detected biomarker, wherein the biomarker information comprises one or more scores determined with reference to a severity scale;
storing the biomarker information and the patient information in a memory unit;
operating on the biomarker information and the patient information in the memory unit to determine a lung disease state for the patient; and
providing an output indicative of the so-determined lung disease state;
wherein the patient information a plurality of patient self-reported scores determined with reference to a severity scale, the scores relating to the patient's perceived own symptoms and/or lung function and comprising: an amount of coughing score; an amount of sputum produced score; a texture of sputum produced score; and a color of sputum produced score;
wherein the biomarker information comprises a plurality of scores determined from the sample with reference to a severity scale and relating to the presence of, or a change in expression level of one or more of: C-reactive protein, neutrophil elastase; IL-8; myeloperoxidase; and procalcitonin; and
wherein the severity scale of the patient self-reported scores and the severity scale of the biomarker scores each utilize a same set of discrete numbers.

20. A method of identifying an individual having chronic obstructive pulmonary disorder (COPD) that is responsive to a treatment, the method comprising steps of: determining a COPD state for the individual; providing a treatment appropriate to the COPD state; monitoring the lung disease state according to the method of claim 19; and identifying the individual as responsive to the treatment according to changes in the monitored disease state.

21. A method of assaying the efficacy of a treatment for chronic obstructive pulmonary disorder (COPD) in an individual, said method comprising steps of: identifying an individual having COPD; determining a lung disease state for the individual; providing a treatment; monitoring the COPD state according to the method of claim 19; and identifying the treatment as effective according to changes in the monitored disease state.

\* \* \* \* \*